(12) United States Patent
Kankan et al.

(10) Patent No.: US 8,691,995 B2
(45) Date of Patent: Apr. 8, 2014

(54) PROCESS

(75) Inventors: Rajendra Narayanrao Kankan, Mumbai (IN); Srinivas Laxminarayan Pathi, Bangalore (IN)

(73) Assignee: Cipla Limited, Mumbai (IN)

( * ) Notice: Subject to any disclaimer, the term of this patent is extended or adjusted under 35 U.S.C. 154(b) by 1653 days.

(21) Appl. No.: 11/721,874

(22) PCT Filed: Dec. 15, 2005

(86) PCT No.: PCT/GB2005/004861
§ 371 (c)(1),
(2), (4) Date: Aug. 28, 2007

(87) PCT Pub. No.: WO2006/064249
PCT Pub. Date: Jun. 22, 2006

(65) Prior Publication Data
US 2010/0016605 A1    Jan. 21, 2010

(30) Foreign Application Priority Data

Dec. 16, 2004  (IN) .......................... 1350/MUM/2004

(51) Int. Cl.
*C07D 401/12* (2006.01)
(52) U.S. Cl.
USPC .................................................... 546/273.7
(58) Field of Classification Search
USPC .................................................... 546/273.7
See application file for complete search history.

(56) References Cited

U.S. PATENT DOCUMENTS

| 4,758,579 A | 7/1988 | Kohl et al. |
| 6,933,389 B2 | 8/2005 | Reddy et al. |

FOREIGN PATENT DOCUMENTS

| EP | 0 166 287 | | 1/1986 |
| EP | 0 533 790 | | 3/1993 |
| EP | 1 518 857 | A1 | 3/2005 |
| JP | S6122079 | A | 7/1993 |
| JP | 2000502101 | A | 2/2002 |
| JP | 2004524303 | A | 8/2004 |
| WO | WO 91/19710 | | 12/1991 |
| WO | 9722603 | A1 | 6/1997 |
| WO | WO 97/29103 | | 8/1997 |
| WO | 9809962 | A1 | 3/1998 |
| WO | 0104109 | A1 | 1/2001 |
| WO | WO 01/04109 | A1 | 1/2001 |
| WO | WO 02/28852 | A1 | 4/2002 |
| WO | 02062786 | A1 | 8/2002 |
| WO | WO 02/062786 | A1 | 8/2002 |
| WO | 2004035565 | A1 | 4/2004 |
| WO | 2004056804 | A2 | 7/2004 |
| WO | 2004063188 | A1 | 7/2004 |

OTHER PUBLICATIONS

Foreign communication from a related counterpart application—International Search Report, PCT/GB2005/004861, Aug. 11, 2006, 5 pgs.

Foreign communication from a related counterpart application—International Preliminary Report on Patentability, PCT/GB2005/004861, Jun. 19, 2007, 10 pgs.

Kohl, Bernard, et al, "(H+,K+)—ATPase inhibiting 2-[(2-pyridylmethyl)sulfinyl]benzimidazoles. 4. A novel series of dimethoxypyridyl-substituted inhibitors with enhanced selectively. The selection of pantoprazole as a clinical candidate," Journal of Medicinal Chemistry, 1992, vol. 35, No. 6, pp. 1049-1057 plus Japanese cover page, American Chemical Society.

The Chemical Society of Japan ed., Hyojun Kagaku Yogo Jiten (Standard Dictionary of Chemical Terms), Maruzen Co., Ltd., 1991, p. 683, 'One-Pot Reaction'.

*Primary Examiner* — Patricia L Morris

(74) *Attorney, Agent, or Firm* — Conley Rose, P.C.; Rodney B. Carroll

(57) ABSTRACT

A one-pot process for the preparation of pantoprazole sodium by reacting 2-chloro methyl 3,4-dimethoxy pyridine hydrochloride with 2-mercapto-5-difluoromethoxy benzimidazole in an organic solvent system in presence of a phase transfer catalyst and further treating with aqueous sodium hypohalite solution comprising sodium hydroxide to obtain pantoprazole sodium in high yield and purity. The process for conversion of pantoprazole sodium to pantoprazole sodium sesquihydrate and also pantoprazole sodium monohydrate are also disclosed herein.

20 Claims, No Drawings

PROCESS

CROSS-REFERENCE TO RELATED APPLICATIONS

This application is a filing under 35 U.S.C. 371 of International Application No. PCT/GB2005/004861 filed Dec. 15, 2005, entitled "Process," claiming priority of Indian Patent Application No. 1350/MUM/2004 filed Dec. 16, 2004, which applications are incorporated by reference herein in their entirety.

FIELD OF THE INVENTION

The present invention relates to a process for the preparation of pantoprazole sodium. More particularly, the invention relates to a one-pot process for the preparation of pantoprazole sodium in high yields and purity. The present invention further relates to process for conversion of pantoprazole sodium to pantoprazole sodium sesquihydrate, and also to pantoprazole sodium monohydrate, in good yields.

BACKGROUND OF THE INVENTION

"Pantoprazole" is the international non-proprietary name of a substituted benzimidazole (5-(difluoromethoxy)-2-[[(3,4-dimethoxy-2-pyridinyl)methyl]sulfinyl]-1H-benzimidazole). It is a compound that inhibits gastric acid secretion. Pantoprazole sodium is a proton pump inhibitor (PPI) used to treat ulcers, gastroesophageal reflux disorder (GERD), erosive esophagitis and Zollinger-Ellison syndrome. It works by blocking acid production in the stomach. It may be used in combination with antibiotics (e.g., amoxicillin, clarithromycin) to treat certain types of ulcers.

The complete pharmacological and therapeutic effect for pantoprazole can be achieved in the acid secreting parietal cells. By means of a feed back mechanism, this effect is diminished at the same rate as acid secretion is inhibited. As with other proton pump inhibitors and H2 Receptor inhibitors, treatment with pantoprazole causes reduced acidity in the stomach causing a reversible increase in gastrin in proportion to the reduction in acidity. Pantoprazole sodium can be represented by the following structural formula.

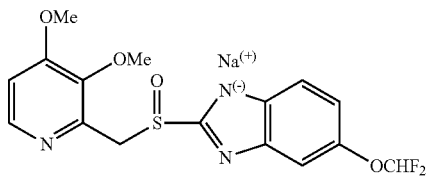

Pantoprazole was disclosed for the first time in European patent application EP0166287.

In one of the processes described in this patent application, 2-chloromethyl-3,4-dimethoxy pyridine was reacted with 2-mercapto-5-difluoromethoxy benzimidazole to prepare a precursor sulfide, which was isolated and oxidized by using metachloroperbenzoic acid to yield pantoprazole base in a yield of 102% by weight with respect to 2-chloromethyl-3,4 dimethoxy pyridine.

PCT Application WO 97/29103 discloses the preparation of pantoprazole by coupling carbonyl fragments to form the sulfoxide precursor, which was further cyclised to obtain pantoprazole base.

PCT Application WO 02/28852 discloses synthesis of pantoprazole and the preparation of key intermediates useful in its synthesis. Pantoprazole base was prepared by oxidation of the chloro derivative of pantoprazole using ammonium per molybdate or ammonium per tungstate in the presence of hydrogen peroxide. Further the chloro group in the resulting product was replaced by methoxy group to obtain pantoprazole base, the yield being about 70% by weight of the pyridine precursor.

PCT Application WO 02/062786 discloses a process for preparation of pantoprazole base by oxidizing the precursor of pantoprazole (i.e. sulfide) using tertiary butyl hydroperoxide and oxone in yield of about 79% weight percent of the sulfide intermediate.

WO 91/19710 discloses pantoprazole sodium sesquihydrate and their typical characteristics.

U.S. Patent 04/0186139A1 describes the preparation of Crystalline Form-I of pantoprazole sodium sesquihydrate from pantoprazole free base by precipitation using various solvents.

It is evident from the teachings of the prior art that multiple steps are required for the synthesis of pantoprazole sodium. Also the intermediates involved for the synthesis need to be isolated at various steps, and further purification is required to get the desired purity of the final product. The use of multiple steps in the prior art results in a lower yield of pantoprazole sodium.

The prior art methods described above also involves the use of many hazardous reagents like hydrogen peroxide, metachloroperbenzoic acid, etc. Thus the processes from the prior art are unable to provide an environmentally safe and industrially applicable process with substantial yields.

OBJECT OF THE INVENTION

It is an object of the invention to solve the problems in the prior art. More particularly it is an object of the present invention to provide an industrially viable and economically feasible process, thereby eliminating the above-mentioned shortcomings.

A further object of the present invention is to provide a one pot process for the synthesis of pantoprazole sodium without the isolation and purification of the intermediates involved in the process.

A further object of the present invention is to provide a process, which avoids the use of hazardous reagents.

Yet another object of the present invention is to provide a industrially viable process for synthesis of pantoprazole sodium in a high yield and good purity and overcoming the shortcomings as described in the prior art.

Another object of the present invention is to provide a process for conversion of pantoprazole sodium to pantoprazole sesquihydrate.

Yet another object of the present invention is to provide a process for conversion of pantoprazole sodium to pantoprazole monohydrate.

SUMMARY OF THE INVENTION

The present invention discloses a novel one-pot process for the synthesis of pantoprazole sodium by reacting 2-chloro methyl 3,4-dimethoxy pyridine hydrochloride with 2-mercapto-5-difluoromethoxy benzimidazole in an organic solvent system in presence of a phase transfer catalyst and further treating with aqueous sodium hypohalite solution to obtain pantoprazole sodium in high yield and purity. The present invention further discloses a process for conversion of pantoprazole sodium to pantoprazole sodium sesquihydrate and also the conversion to pantoprazole sodium monohydrate.

According to one aspect of the invention there is provided a process for preparation of pantoprazole sodium, comprising the steps of:
(a) reacting 2-chloromethyl 3,4 dimethoxy pyridine hydrochloride with 2-mercapto-5-difluoromethoxy benzimidazole in an organic solvent and aqueous sodium hydroxide solution in presence of a phase transfer catalyst to obtain pantoprazole sulphide; and
(b) treating said pantoprazole sulphide obtained in step (a) with an aqueous sodium hypohalite solution containing sodium hydroxide to yield pantoprazole sodium.

The use of a phase transfer catalyst has not previously been described for the preparation of pantoprazole intermediates. It is possible for the pantoprazole sulphide to be isolated between steps (a) and (b). However, this is not preferred, as it is possible to improve the yield and purity of the pantoprazole sodium by taking the pantoprazole sulfide in the organic phase formed in step (a), and treating it with the hypohalite solution. Thus, in the preferred embodiment, there is no isolation of the pantoprazole sulphide between steps (a) and (b). In the most preferred embodiment, the process is a one-pot process; this means that the steps (a) and (b) are both carried out in the same reaction pot.

According to another aspect of the present invention, there is provided a process for converting pantoprazole sodium to pantoprazole sodium sesquihydrate, comprising the steps of
(i) dissolving pantoprazole sodium in acetone;
(ii) co-distilling with ethyl acetate till precipitation occurs;
(iii) cooling the suspension to room temp;
(iv) adding water in a quantity sufficient enough to form the sesquihydrate;
(v) stirring at room temp;
(vi) chilling the reaction mixture; and
(vii) isolating pantoprazole sodium sesquihydrate by filtration and drying.

According to another aspect of the present invention, there is provided a process for converting pantoprazole sodium to pantoprazole sodium monohydrate, comprising the steps of:
(i) dissolving pantoprazole sodium in acetone;
(ii) co-distilling with ethyl acetate till precipitation occurs;
(iii) cooling the suspension to room temp; chilling the reaction mass; and
(iv) isolating pantoprazole sodium monohydrate by filtration and drying.

Furthermore, using the process according to the present invention, it is possible to obtain pantoprazole sodium in a form that is purer than has been possible in accordance with the prior art. Thus, in accordance with another aspect of the invention, there is provided pantoprazole sodium having a purity level above 97.0 wt %. More preferably the purity level is at least, or above, 97.5 wt %. Still more preferably the purity level is at least or above 98.0 wt %. Still more preferably the purity level is at least or above 98.5 wt %. Still more preferably the purity level is at least or above 98.5 wt %. Still more preferably the purity level is at least or above 99.0 wt %. Most preferably, the purity level is at least or above 99.5 wt % (This means, for example, that the pantoprazole API produced in accordance with the process of the invention consists of at least 99.5 wt % pantoprazole sodium, and not more than 0.5 wt % impurities). The maximum purity is typically 99.7 wt % or 99.8 wt %.

In accordance with the invention, pantoprazole sodium monohydrate and pantoprazole sodium monohydrate can be produced in the same purity as the pantoprazole sodium.

Thus, in accordance with another aspect of the invention, there is provided pantoprazole sodium monohydrate or sesquihydrate having a purity level above 97.0 wt %. More preferably the purity level is at least, or above, 97.5 wt %. Still more preferably the purity level is at least or above 98.0 wt %. Still more preferably the purity level is at least or above 98.5 wt %. Still more preferably the purity level is at least or above 98.5 wt %. Still more preferably the purity level is at least or above 99.0 wt %. Most preferably, the purity level is at least or above 99.5 wt %. The maximum purity is typically 99.7 wt % or 99.8 wt %.

DETAILED DESCRIPTION OF THE INVENTION

The present invention relates to a process for the synthesis of pantoprazole sodium of Formula (I).

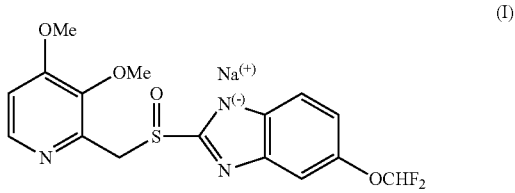

The present invention provides a process for the preparation of pantoprazole sodium wherein 2-chloromethyl-3,4-dimethoxypyridine hydrochloride (III) is reacted with 2-mercapto-5-difluoromethoxy benzimidazole (IV) in an organic solvent system and water containing an inorganic base, in presence of a phase transfer catalyst. This yields pantoprazole sulfide, which is converted to pantoprazole sodium without isolation of the sulfide.

The temperature of the reaction preferably ranges from 0° C. to the reflux temperature of the solvent used, and more preferably ranges from 25-30° C.

The compound of the formula (III) may be used directly as starting material or optionally synthesized by reacting 2-hydroxymethyl 3,4-dimethoxy pyridine (II) with a chlorinating agent, preferably thionyl chloride, at a temperature preferably ranging from −5° C. to ambient temperature preferably 0 to 5° C. Water may be added to the reaction mass and this reaction mass may be used as such without isolation of the compound of formula (III). Thus, the steps of the formation of compound (III), and its conversion to pantoprazole sodium, may all be carried out with advantage in a one-pot reaction.

In another aspect, the present invention provides the use of phase transfer catalyst, which is advantageous as it helps in the progress of the reaction, which involves biphasic medium. The phase transfer catalyst is preferably selected from the group consisting of tetrabutyl ammonium bromide, tetrabutyl ammonium chloride, benzyltriethyl ammonium chloride, methyltrioctyl ammonium chloride, hexadecyltrimethyl ammonium chloride, crown ethers, and mixtures thereof. Most preferably, the phase transfer catalyst is tetrabutyl ammonium bromide.

The solvent system used in the process of present invention preferably comprises water immiscible organic solvent and water containing an inorganic base. The preferred water immiscible organic solvent is an aliphatic chlorinated hydrocarbon. Preferably, the water immiscible solvent is selected from the group consisting of methylene dichloride, carbon tetrachloride, cyclohexane, chloroform and dichloroethane.

The inorganic base employed in the present invention may be an alkaline metal hydroxide or carbonate, most preferably sodium hydroxide.

The process of the present invention is advantageously carried out in one pot without the isolation of any intermediates as illustrated in Scheme below.

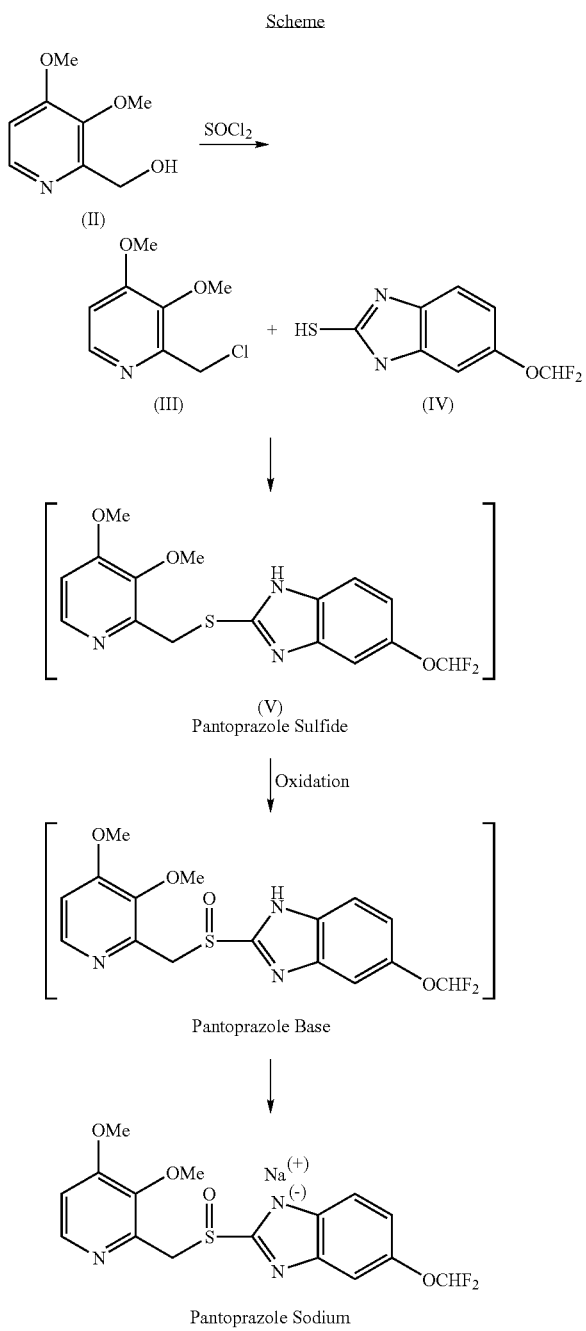

The intermediates (V) pantoprazole sulfide and pantoprazole base as shown in the scheme were not isolated during the process of the present invention. In particular, they were not subjected to any purification. Further, the pantoprazole sulfide obtained in situ was oxidized using aqueous sodium hypohalite solution preferably an aqueous solution of sodium hypochlorite with a strength from 2-14%, and having a sodium hydroxide content from 0.5 to 10%, more preferably from 1.0 to 3.0%. We prefer that the sodium hydroxide content is at least 2%. Most preferably, the sodium hydroxide content is from 2.0 to 2.3%. The oxidation of the pantoprazole sulfide is preferably carried out at a temperature ranging from 0° C. to ambient temperature, more preferably 5-8° C. The resulting reaction mass was cooled to afford pantoprazole sodium.

The strength of hypohalite is denoted in the form of concentration. Thus, for example, a concentration of 2-14% of sodium hypohalite means 2-14% of $OX^-$ with counter ion $Na^+$ in water, X being halide ion. The reference to the sodium hydroxide content means the weight of pure sodium hydroxide per weight of aqueous sodium hypochlorite solution.

Ambient temperature, as used in this specification, means temperatures ranging from 25° C. to 30° C.

The pantoprazole sodium formed by the method according to the invention may be used to make pharmaceutical formulations containing pantoprazole sodium, using conventional formulating methods.

In accordance with another aspect of the invention, pantoprazole sodium (which is preferably obtained by the process of the present invention) is further converted to pantoprazole sodium sesquihydrate by dissolving it in acetone and replacing the solvent by ethyl acetate followed by co-distilling with ethyl acetate and isolating the sesquihydrate from the ethyl acetate-water mixture; this mixture contains water in a quantity sufficient enough to form the sesquihydrate In accordance with another aspect of the invention, pantoprazole sodium (which is preferably obtained by the process of the present invention) is converted to pantoprazole sodium monohydrate by stirring in ethyl acetate.

The pantoprazole sodium obtained by the process of the present invention has a very high level of purity and the known impurities like sulfone, sulfone N-oxide, and sulfide were below 0.15% wt % and individual unknown impurities were less than 0.1% wt %.

EXAMPLES

The invention will now be further described with reference to the following examples, which further illustrate the invention.

Example 1

Preparation of 5-(difluoromethoxy)-2[[(3,4-dimethoxy-2-pyridinyl)methyl]sulfinyl]-1H benzimidazole sodium 2-Chloromethyl-3,4-dimethoxy pyridine hydrochloride (50 gms), 2-mercapto-5-difluoromethoxy benzimidazole (50 gms) and Tetra butyl ammonium bromide (2 gms) were added under stirring to dichloromethane (300 ml) followed by solution of sodium hydroxide (37.5 gms) in 120 ml water. The contents were then stirred at 25-30° C. for about 12 hours. After reaction completion, the dichloromethane layer was separated, then the aqueous layer was extracted with dichloromethane (60 ml) twice. The organic layers were combined together, water washed and distilled to about 250 ml and cooled to 0° C. 3.5% aqueous sodium hypochlorite solution (464 g) having a sodium hydroxide content of 2.2% was added to the reaction mass, which was maintained at 5-8° C. for about 6 hours. After completion of the reaction; the reaction mass was further cooled to 0 to 5° C. The resulting solid was then filtered and washed with cold acetone (about 100 ml) and dried under vacuum at 35-40° C. to give pantoprazole sodium (75 gms, 83%) of purity greater than 99.5%.

Example 2

Preparation of 5-(difluoromethoxy)-2[[(3,4-dimethoxy-2-pyridinyl)methyl]sulfinyl]-1H benzimidazole sodium 2-hydroxymethyl-3,4-dimethoxy pyridine hydrochloride (45.8 g) was taken in dichloromethane (300 ml). Thionyl chloride (30.3 gms.) was added at about 0 to 5° C. and reaction mass was further stirred at 10-15° C. for 1 hour. After reaction completion, purified water (100 ml) was added maintaining the reaction temperature between 15-20° C. To this reaction mass, 2-mercapto 5-difluoromethoxy benzimidazole (50 gms) and tetra butyl ammonium bromide (2 gms) were added. The contents were cooled to 10° C. and pH of the reaction mass was adjusted to 10-11 using aqueous sodium hydroxide solution (30% solution) and the contents were stirred at 25-30° C. for 12 hours. After completion of the reaction, dichloromethane layer was separated and the aqueous layer was extracted with dichloromethane (60 ml) twice. The combined organic layer was washed with purified water (150 ml) twice. The dichloromethane layer was then cooled to 0° C., 3.5% aqueous sodium hypochlorite solution (464 g) having sodium hydroxide content of 2.1% was added to the reaction mass, and maintained at 5-8° C. for about 6 hours. After the completion of the reaction, the reaction mass was cooled to 0 to 5° C. and the resulting solid was filtered and washed with cold acetone (about 100 ml) and dried under vacuum at 35-40° C. to give pantoprazole sodium (72 gms, 79.6%) of purity greater than 99.5%.

Example 3

Preparation of Pantoprazole Sodium Sesquihydrate

Pantoprazole sodium (75 gms) as prepared according to Example-1 or Example-2 was dissolved in 375 ml of acetone at about 50-55° C., charcoal (5 gms) was added and the reaction mass was stirred for 15 minutes and clarified hot. The resulting clear filtrate was concentrated to approx. volume of 150 ml, ethyl acetate (400 ml) was added and distillation was continued until precipitation was observed in the reaction mass. The reaction mass was cooled to room temperature and water (4.2 ml) was added, the suspension was stirred for 1 hr. and later chilled and stirred at 0-5° C. for 1 hr. The product was the isolated by filtration and was dried at 40-45° C. under vacuum to give pantoprazole sodium sesquihydrate (68 gms.) having a moisture content of 6.5%.

Example 4

Preparation of Pantoprazole Sodium Monohydrate

Pantoprazole sodium (75 gms) as prepared according to Example-1 or Example-2 was dissolved in 375 ml of acetone at about 50-55° C., charcoal (5 gms) was added and the reaction mass was stirred for 15 minutes and filtered hot. The resulting clear filtrate was concentrated to approx. volume of 150 ml and ethyl acetate (400 ml) was added, distillation was continued until precipitation was observed in the reaction mass. The reaction mass was cooled to room temperature and the suspension was stirred for 1 hr. and later chilled and stirred at 0-5° C. for 1 hr. The product was isolated by filtration and dried at 40-45° C. under vacuum to give pantoprazole sodium monohydrate (64 gms.) having a moisture content of 4.5%.

Example 5

Preparation of Pantoprazole Sodium Sesquihydrate

Pantoprazole sodium (75 gms) as prepared according to Example-1 or Example-2 was dissolved in 375 ml of acetone at about 50-55° C., and reaction mass was stirred for 15 minutes and filtered hot. The resulting clear filtrate was cooled to about 25-30° C. and 375 ml of diisopropyl ether was added under stirring the resulting product was filtered and dried at 35-40° C. to give pantoprazole sodium (72 gms). The dried product was stirred in mixture of 216 ml ethylacetate and 3.6 ml purified water for 1 hr.; the slurry was then chilled and stirred at 0-5° C. for about 1 hr. The product was filtered and dried at 40-45° C. under vacuum to give pantoprazole sodium sesquihydrate (68 gms.) having a moisture content of 6.5%.

Example 6

Preparation of Pantoprazole Sodium Monohydrate

Pantoprazole sodium (75 gms) as prepared according to Example-1 or Example-2 was dissolved in 375 ml of acetone at about 50-55° C., and reaction mass was stirred for 15 minutes and filtered hot. The resulting clear filtrate was cooled to about 25-30° C. and 375 ml of diisopropyl ether was added the resulting solid was filtered and dried under vacuum at 35-40° C. to give pantoprazole sodium (72 gms). The dried product was stirred in 216 ml ethylacetate for 1 hr. and was then chilled and stirred at 0-5° C. for 1 hr. The product was isolated by filtration and dried at 40-45° C. under vacuum to give pantoprazole sodium monohydrate (68 gms.) having a moisture content of 4.5%.

The invention claimed is:

1. A process, comprising the steps of:
    (a) reacting 2-chloromethyl 3,4 dimethoxy pyridine hydrochloride with 2-mercapto-5-difluoromethoxy benzimidazole in an organic solvent and an inorganic base in the presence of a phase transfer catalyst to obtain pantoprazole sulphide; and
    (b) treating said pantoprazole sulphide formed in step (a) with an aqueous sodium hypohalite solution containing sodium hydroxide to yield pantoprazole sodium, without isolating said pantoprazole sulphide in step (a).

2. The process according to claim 1, wherein the inorganic base is in the form of a solution of said base in water.

3. The process according to claim 1, wherein said inorganic base is selected from an alkaline metal hydroxide or carbonate.

4. The process according to claim 1, wherein the inorganic base is sodium hydroxide.

5. The process according to claim 1, wherein the pantoprazole sulphide formed in step (a) is obtained in an organic phase, and said pantoprazole sulphide in the organic phase is treated with the hypohalite solution.

6. The process according to claim 1, wherein steps (a) and (b) are carried out in one-pot reaction.

7. The process according to claim 1, wherein the organic solvent in steps (a) and step (b) is a water immiscible organic solvent, or a mixture of water immiscible organic solvents.

8. The process according to claim 1, wherein said organic solvent is an aliphatic chlorinated hydrocarbon.

9. The process according to claim 1, wherein said water immiscible organic solvent is selected from the group consisting of methylene dichloride, carbon tetrachloride, cyclohexane, chloroform, dichloroethane.

10. The process according to claim 1, wherein said phase transfer catalyst used is selected from the group consisting of tetrabutylammonium bromide, tetrabutylammonium chloride, tetrabutylammonium fluoride, benzyltriethylammonium chloride, methyltrioctylammonium chloride hexadecyltrimethylammonium chloride and crown ethers, or mixtures thereof.

11. The process according to claim 1, wherein the concentration of said aqueous sodium hyophalite is from 2 to 14%.

12. The process according to claim 1, wherein the content of said sodium hydroxide in aqueous solution of sodium hypochlorite is at least 2.0%.

13. The process of claim 1, further comprising the steps of;
(c) dissolving pantoprazole sodium in acetone;
(d) co-distilling with ethyl acetate till precipitation occurs;
(e) cooling the suspension to room temp;
(f) adding water in a quantity sufficient enough to form the sesquihydrate;
(g) stirring at room temp;
(h) chilling the reaction mixture; and
(i) isolating pantoprazole sodium sesquihydrate by filtration and drying.

14. The process of claim 1, comprising the steps of:
(c) dissolving pantoprazole sodium in acetone;
(d) co-distilling with ethyl acetate till precipitation occurs;
(e) cooling the suspension to room temp;
(f) chilling the reaction mass; and
(g) isolating pantoprazole sodium monohydrate by filtration and drying.

15. The process according to claim 13, wherein the concentration of said aqueous sodium hyophalite is from 2 to 14%.

16. The process according to claim 15, wherein the content of said sodium hydroxide in aqueous solution of sodium hypochlorite is at least 2.0%.

17. The process according to claim 16, wherein said organic solvent is an aliphatic chlorinated hydrocarbon.

18. The process according to claim 17, wherein the pantoprazole sulphide formed in step (a) is obtained in an organic phase, and said pantoprazole sulphide in the organic phase is treated with the hypohalite solution.

19. The process according to claim 18, wherein steps (a) and (b) are carried out in one-pot reaction.

20. The process according to claim 19, wherein said water immiscible organic solvent is selected from the group consisting of methylene dichloride, carbon tetrachloride, cyclohexane, chloroform, dichloroethane; and said phase transfer catalyst used is selected from the group consisting of tetrabutylammonium bromide, tetrabutylammonium chloride, tetrabutylammonium fluoride, benzyltriethylammonium chloride, methyl trioctylammonium chloride hexadecyltrimethylammonium chloride and crown ethers, or mixtures thereof.

* * * * *

UNITED STATES PATENT AND TRADEMARK OFFICE
CERTIFICATE OF CORRECTION

PATENT NO. : 8,691,995 B2
APPLICATION NO. : 11/721874
DATED : April 8, 2014
INVENTOR(S) : Kankan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1815 days.

Signed and Sealed this

Twenty-ninth Day of September, 2015

Michelle K. Lee
*Director of the United States Patent and Trademark Office*